United States Patent
Dobrowolski et al.

(10) Patent No.: US 12,350,373 B2
(45) Date of Patent: Jul. 8, 2025

(54) NANO-SEEDING

(71) Applicant: Bayer Aktiengesellschaft, Leverkusen (DE)

(72) Inventors: Adrian Dobrowolski, Remscheid (DE); Giovanni Maria Maggioni, Cologne (DE); Michal Sowa, Wuppertal (DE); Clemens Bothe, Leverkusen (DE); Eva Esser, Duesseldorf (DE); Christoph Nueboldt, Cologne (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 280 days.

(21) Appl. No.: 17/932,757

(22) Filed: Sep. 16, 2022

(65) Prior Publication Data
US 2023/0098132 A1 Mar. 30, 2023

(30) Foreign Application Priority Data

Sep. 24, 2021 (EP) .................................... 21198775
Apr. 29, 2022 (EP) .................................... 22170761

(51) Int. Cl.
*A61K 9/16* (2006.01)

(52) U.S. Cl.
CPC .................................. *A61K 9/1688* (2013.01)

(58) Field of Classification Search
CPC ... A61K 9/1688; A61K 9/1652; A61K 9/1694
See application file for complete search history.

(56) References Cited

U.S. PATENT DOCUMENTS

2009/0087492 A1   4/2009   Johnson et al.

FOREIGN PATENT DOCUMENTS

WO       02/04473 A1   *   1/2002
WO    2021069350 A1        4/2021

OTHER PUBLICATIONS

Ikeda et al., Effect of Hydrophobically Modified HydroxyPropyl MethylCellulose on Crystallization Supersaturated Solutions of Indomethacin, 2375 Chemical & Pharmaceutical Bulletin, 42, November, No. 11, Tokyo, JP. (Year: 1994).*
Extended European Search Report for European Patent Application No. 21198775.5, mailed Mar. 9, 2022.
Perry Chemical Engineering Handbook, 8th Edition, McGraw-Hill, 2007.
Iggland, Martin, and Marco Mazzotti. "A population balance model for chiral resolution via Viedma ripening." Crystal growth & design, (2011), vol. 11, No. 10: 4611-4622.

(Continued)

*Primary Examiner* — Carlos A Azpuru
(74) *Attorney, Agent, or Firm* — Ann H. Inglett

(57) ABSTRACT

What is described herein relates to a method for generating micro-particles comprising the steps of
  a) providing a homogenous supersaturated solution of a substance in a crystallization medium
  b) providing a seeding material characterized by a nano-particle size of a d50 between 10 nm and 999 nm comprising at least one stabilizer, wherein said seeding material is of the same substance as the substance of the homogenous supersaturated solution of step a)
  c) bringing the homogenous supersaturated solution in contact with the seeding material,
optionally isolating micro-particles.

11 Claims, 8 Drawing Sheets

(56) References Cited

OTHER PUBLICATIONS

Filters and Filtration Handbook, 6th edition, Trevor and Chase, Butterworth-Heinemann 2015, pp. 22-33.
Dann, Sandra E. "Solid state structure." In Reactions and Characterization of Solids, 2000, pp. 1-204.
Chauhan, "Powder XRD Technique and its Applications in Science and Technology," Journal of Analytical & Bioanalytical Techniques, J Anal Bioanal Tech, vol. 5, Issue 5, 2014, 5 pages.
Ikeda et al., "Effect of Hydrophobically-Modified Hydroxypropyl Methylcellulose on the Crystallization from Supersaturated Solutions of Indomethacin," Chemical and Pharmaceutical Bulletin, vol. 42, No. 11, Nov. 1994, pp. 2320-2326.

\* cited by examiner

NANO-SEEDING

CROSS REFERENCE TO RELATED APPLICATIONS

This application claims priority from EP 21198775.5 filed 2021 Sep. 24 and EP 22170761.5 filed 2022 Apr. 29 the contents of which are incorporated herein by reference in their entireties.

BACKGROUND

Field

The present invention relates to a nano-seeding process.

Description of Related Art

A significant proportion of active ingredients e.g. of active pharmaceutical ingredients and active agrochemical ingredients have poor solubility and/or require a high bioavailability and short dissolution times. To improve the poor solubility especially in water and optimize high bioavailability and short dissolution times, a commonly accepted method is to reduce the particle size of the active ingredients to create a large surface-to-volume ratio and hence a high solubility particle interface.

A well-known method to produce microparticles is dry-milling. However, this method has some limitations, such as high energy consumption, low yields, formation of encrustations, and difficult-to-control particle sizes and surface properties, which complicate microparticle production and consistent quality. Therefore, there is a need for an improved process for generating micro-particles.

This need is met by a simplified process for generating micro-particles.

According to a first aspect what is described herein relates to a process for generating micro-particles comprising the steps of
  a) providing a homogenous supersaturated solution of a substance in a crystallization medium
  b) providing a seeding material characterized by a nano-particle size of a d50 between 10 nm and 999 nm as measured by Dynamic Light Scattering (DLS), laser diffraction or electron microscopy comprising at least one stabilizer, wherein said seeding material is of the same substance as the substance of the homogenous supersaturated solution of step a)
  c) bringing the homogenous supersaturated solution in contact with the seeding material,
  d) optionally isolating micro-particles.

According to a second aspect what is described herein relates to the use of nanoparticles of a d50 between 10 nm and 999 nm as measured by Dynamic Light Scattering (DLS), laser diffraction or electron microscopy as seeding material in cooling crystallization.

BRIEF DESCRIPTION OF THE DRAWINGS

Figures

DETAILED DESCRIPTION

Definitions

Figure 1:
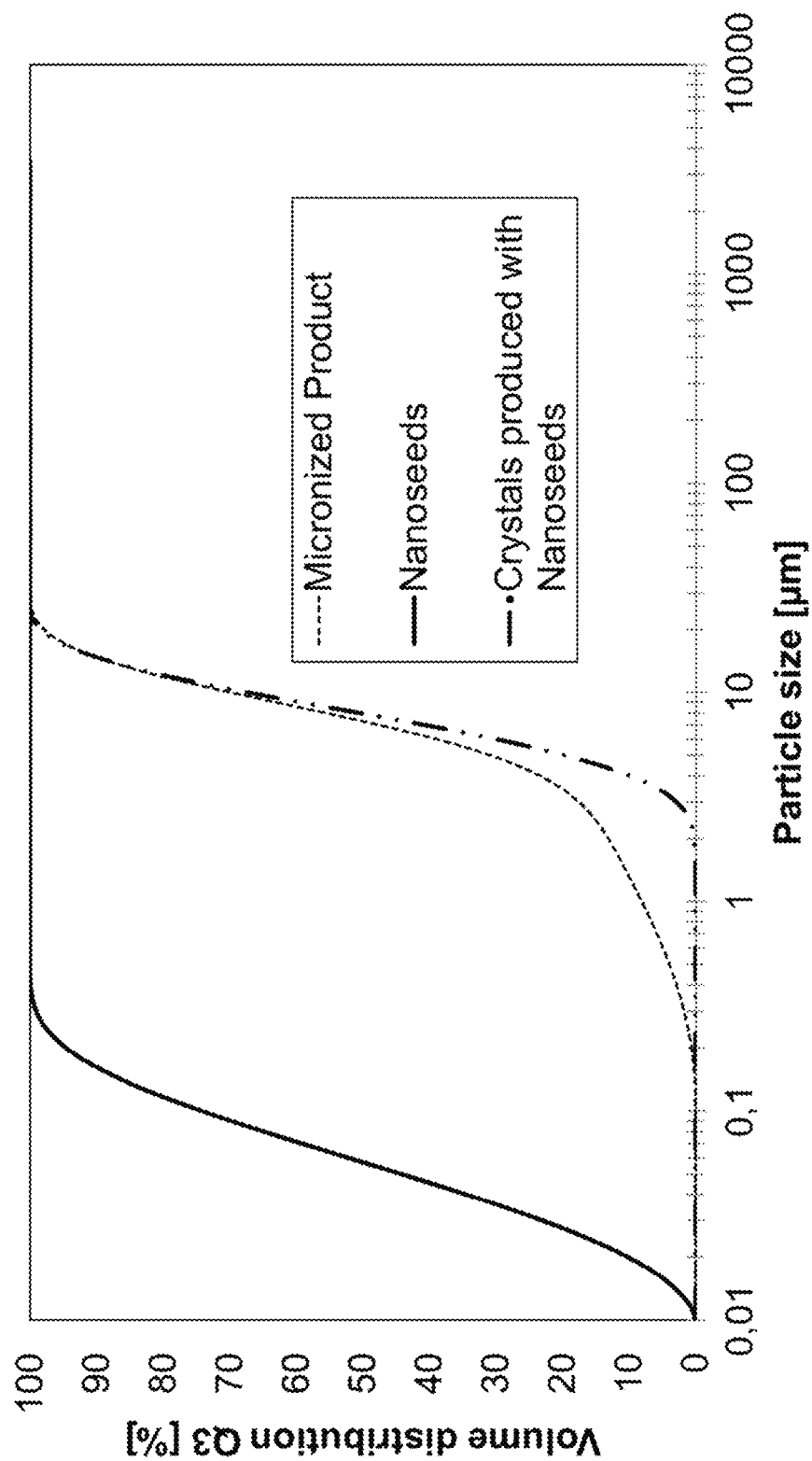
FIG. 1 shows that using nano seeding material leads to micro-particles comparable to micro-particles generated with conventional processes.

As used herein, the term "particle" refers to a solid, gel, or semisolid material having a relatively small size.

As used herein the term "micro-particle" which is used synonymously with microparticle refers to particles having an average particle size of between >999 nm to 100 µm.

Preferably the micro-particles obtained with the process for generating micro-particles described herein have an average d90 of between 2 µm and 50 µm, more preferably between 2 µm and 30 µm, most preferably between 2 µm and 20 µm.

As used herein the term "nano" refers to particles having an average particle size—i.e. d50 of the distribution—of ≥10 nm to ≤999 nm, preferably the nanoparticles have an d90— of ≥10 nm to ≤999 nm, Herein the nanoparticles (also termed nano-particles) have a particle size distribution of d50 of ≥10 nm to ≤999 nm preferably ≥10 nm to <400 nm especially preferred ≥10 nm to <200 nmThe particle size distribution can be determined by methods known in the art such as laser diffraction or Dynamic Light Scattering (DLS). The term d50 or d90 means that 50% or 90% of the total product volume consists of particles smaller than the given value for d50 or d90. The given particle size corresponds to the hydrodynamic particle size when determined by DLS (dynamic light scattering), laser diffraction or electron microscopy and for all methods an equivalent size for spheres is given and meant here. A person skilled in the art is capable of choosing technical equipment suitable for achieving a respective d50 or d90 value. For example it is clear to a skilled person that using an agitated ball mill will result in a smaller d50 and d90 values than using a planetary ball mill, especially if the agitated ball mill is cooled.

If Laser diffraction was used to determine the particle size said laser diffraction was performed in a Malvern Mastersizer 3000. A spatula tip of the powder sample was suspended in 10 ml of deionized water and a droplet of Tween80 was added as dispersant. The sample was first mixed with the spatula then dispersed with a pipette. The Mastersizer 3000 was equipped with a Hydro MV unit, where deionized water was provided to disperse and dilute the sample further. The dispersed sample was added to the Hydro MV unit until the obscuration reached 5%. The mixer of the Hydro MV unit was set to 2500 rpm. The first three measurements were performed with red and blue laser lights using the Mie light scattering model. Three measurements were performed. In addition ultrasonic was applied for 1, 3 and 5 min. After each sonification time one measurement was performed. The particle size typically did not change after 3 minutes of sonification. Therefore this value was taken for the comparison of experiments.

X-Ray diffraction (XRD) on the other hand can be used to determine the atomic and molecular structure of a crystal. XRD is based on the fact that a crystalline structure causes a beam of incident X-rays to diffract into many specific directions. By measuring the angles and intensities of these diffracted beams, a crystallographer can produce a three-dimensional picture of the density of electrons within the crystal. From this electron density, the mean positions of the atoms in the crystal can be determined, as well as their chemical bonds, their crystallographic disorder, and various other information. (see, for example, Dann, Sandra E. *Reactions and characterization of solids.* Vol. 2. Royal Society of Chemistry, 2000. or Chauhan and Chauhan, J *Anal Bioanal Tech* 2014, 5:5).

As used herein the term "seeding material" refers to nano-particles of the same substance or composition as the micro-particles to be generated by the process described herein. In general the seeding material is analyzed for its quality, purity, and particle size distribution. The quality of the seeding material i.e. the polymorphism and/or pseudo-polymorphism can be determined, e.g. by means of X-ray diffraction and/or Raman and/or IR spectroscopy. The size distribution of the seeding material can be determined by laser diffraction and/or dynamic light scattering. The purity of the seeding material can be determined e.g. by chromatography.

Homogenous as used herein refers to the fact that a material is uniform in appearance. When referring to a solution homogenous therefore means that no distinct solid and liquid phases co-exist.

When referring to a suspension—e.g. after the homogenous supersaturated solution and the seeding material have been brought into contact—"homogenous" is herein meant to be if no spontaneous segregation of particles according to their size can be detected within the suspension and/or if no dead volumes, i.e. portion of reactor where the flow stagnates, can be observed, e.g. by means of visual analysis or tracer-based methods, or predicted, e.g. by means of CFD simulations within 30 min to 2 days after preparation of the solution. The selection of the relevant operating conditions to ensure good miscibility can be assessed by calculating the relevant non-dimensional numbers (e.g. Newton, Reynold, Peclet), which account for the geometric properties of the chosen vessel and impeller. The correlations between such numbers and the relevant operating conditions are tabulated in the relevant literature, e.g. Perry Chemical Engineering Handbook, 8th Edition, McGraw-Hill, 2007.

A skilled person is aware of the fact that upon spontaneous formation of particles, or after their addition through seeding, the supersaturated solution becomes a suspension, i.e. a system where distinct solid and liquid phases co-exist.

As used herein the term "supersaturated" refers to a solution, in which the concentration of a solute exceeds the concentration of its thermodynamically equilibrium value.

The supersaturated homogenous solution used in the process described herein is in the metastable zone width. Metastable zone width as used herein refers to the interval of temperature and concentration in which a solution is supersaturated, but kinetically stable, i.e. the spontaneous appearance and growth of crystals whilst thermodynamically possible, is not observed. In other words, a skilled person is aware of the fact that the metastable zone width refers to the combination of temperature range and concentration range i.e. the zone in which a solution of a given solute is supersaturated but does not yet spontaneously crystallize and is not supersaturated any longer i.e. the addition of seeding material would no longer result in crystal formation. The metastable zone width i.e. the temperature and concentration values for a given solute in a given crystallization medium have to be determined on a case by case basis. A person skilled in the art knows how to perform the required experiments for a given solute in a given crystallization medium. For example, a skilled person would perform a screening of solvents compatibly with chemical constraints such as product degradation followed by screening for the possible presence of (pseudo)polymorphs and measuring the relevant solubilities. Alternatively, computer models can also be exploited to a certain degree to mitigate (but not fully replace) in vitro experiments, e.g. by performing DFT or MD simulations to assess the relative stability of different polymorphs, or by estimating the solubility, e.g. using PC-SAFT and the related theory of groups.

As used herein the term "flowability" refers to powder flow i.e. the capacity to move by flow of loose particulate solids.

A person skilled in the art is aware of the fact that the flowability of a powder depends on various factors such as particle size distribution, particle shape, chemical composition of the particles, moisture and temperature. A Schulze ring shear tester can be used for comparing flowabilities of different powders.

As used herein the term "stabilizer" refers to a polymer that sterically and/or a surfactant that electrostatically or sterically stabilizes the nano-particles.

As used herein the term "active ingredient" refers to an agent, active ingredient, compound, substance, compositions, or mixtures thereof, that provides a pharmacological and/or agrochemical effect.

As used herein the term "crystallization medium" refers to a liquid in which the substance constituting the nano-particles and the to be generated micro-particles is soluble in and from which the substance can crystallize when the medium is supersaturated. A skilled person is aware of the fact that in cases of where more than one active ingredient is present in a given composition e.g. active ingredient combinations in step a) the substance to be crystallized is present as the homogenous supersaturated solution while possible other (active) ingredients in the crystallization medium are present as suspension.

A person skilled in the art knows how to determine a suitable crystallization medium depending on the specific process as well as chemical and regulatory requirements. Standard crystallization media for pharmaceutical and agrochemical relevant substances are, for example, water, methanol, ethanol, acetone, acetic acid, depending on whether an inorganic (water) or organic (other) medium is required, whether the solubility is promoted by protonated (water, alcohols, acids) or non-protonated (acetone or esters) solvents and/or by the presence of H-bonds and/or other coordination groups. In one example described herein the micro-particles were active ingredient micro-particles and were crystallized in acetic acid, where solubility strongly depends on temperature and where the formation of other undesired polymorphs does not take place at the process conditions. In the case of acetylsalicylic acid as active ingredient a mixture of acetic anhydride and acetic acid is used as crystallization medium, due to the requirements of synthesis occurring prior to crystallization. Another known crystallization medium is ethanol.

Detailed Description

As specified above according to a first aspect what is described herein relates to a process for generating micro-particles comprising the steps of
- a) providing a homogenous supersaturated solution of a substance in a crystallization medium
- b) providing a seeding material characterized by a nano-particle size of a d50 between 10 nm and 999 nm as measured by Dynamic Light Scattering (DLS), laser diffraction or electron microscopy comprising at least one stabilizer, wherein said seeding material is of the same substance as the substance of the homogenous supersaturated solution of step a)
- c) bringing the homogenous supersaturated solution in contact with the seeding material,
- d) optionally isolating micro-particles.

The improved process—also termed nano-seeding—for generating microparticles described herein is a shorter, faster, less tedious, less time consuming and less error prone process as it omits the need to perform a micronization step in order to generate homogenous microparticles of a suitable d90 value. This has the advantage that challenges such as caking during micronization of cohesive powder active ingredients (API) which complicates process control due to clogging are no longer of relevance.

Moreover, the improved process for generating microparticles described herein is also more cost effective since the omitted micronization is an energy-intensive process carried out under high pressures (up to 7 bar nitrogen or more) and low loadings. Additionally the improved process for generating microparticles described herein is also more cost effective since the amount of required seeding material for achieving the same particle size (e.g. d90 or d50 etc.) of the generated microparticles is smaller if nano-particles are used compared to a case in which microparticles would be used as seeding material. This effect is more pronounced the smaller the nano-particles are.

In addition, the improved process for generating microparticles gives comparable yields to the methods described in the art for generating microparticles, i.e. it does not suffer the draw-back of other processes omitting micronization such as early termination of the cooling crystallization that show a significant loss of yield. In the nano-seeding process, on the contrary, the final crystallization conditions, e.g. the final temperature can be kept. Consequently, the final yield related to the solubility is also unchanged, which would not occur if early termination was implemented.

Furthermore, the use of nano particles as seeding material increases the likelihood that no long needles will be formed during crystallization, or will be formed to a lesser extent. This can be advantageous in many ways. Needle-shaped powders generally have poorer flowability than spherical or cuboidal powders. In addition, the filterability of these particles from the mother liquor after crystallization may well be improved. The processability of the end product is thus improved.

In accordance with one or more aspects there is provided
1. Method for generating micro-particles comprising the steps of
- a) providing a homogenous supersaturated solution of a substance in a crystallization medium
- b) providing a seeding material characterized by a nano-particle size of a d50 between 10 nm and 999 nm as measured by Dynamic Light Scattering (DLS), laser diffraction or electron microscopy comprising at least one stabilizer, wherein said seeding material is of the same substance as the substance of the homogenous supersaturated solution of step a)
- c) bringing the homogenous supersaturated solution in contact with the seeding material,
- d) optionally isolating micro-particles.
2. In a preferred embodiment, the seeding material is characterized by a nano-particle size of a d90 between 10 nm and 999 nm as measured by Dynamic Light Scattering (DLS), laser diffraction or electron microscopy.
3. Method according to 1 above, wherein the seeding material comprises only one polymer as stabilizer.
4. Method according to 1 above, wherein the seeding material comprises one surfactant and at least one polymer as stabilizer.
5. Method according to 1 above, wherein the seeding material is provided suspended in the crystallization medium or is provided as seeding material obtained by the method described in WO 2021/069350 the content of which is incorporated herein by reference, characterized in that, the seeding material is obtained via
  - A) suspending particles of the substance in an aqueous solution of a polymer;
  - B) drying the mixture obtained after step A);
  characterized in that
  in step A), the d90 value of the particle size distribution is ≤1 μm, and in that
  prior to step B), the particles are contacted with an ionic surfactant
  and wherein the particles of the substance and the polymer are present in a weight ratio of >1:2 to ≤5:1 to each other
6. Method according to 5 above, wherein the seeding material is provided as powder or as tablet, which dissolves readily into seeding material characterized by a nano-particle size of a d50 between 10 nm and 999 nm as measured by Dynamic Light Scattering (DLS), laser diffraction or electron microscopy comprising at least one stabilizer, of step b) upon contact with the homogenous supersaturated solution of step a)
7. Method according to 1 above, wherein the substance provided as homogenous supersaturated solution is an active ingredient and hence the seeding material and any generated micro-particles are active ingredient particles.
8. Method according to 1 above, where after bringing the homogenous supersaturated solution in contact with the seeding material the supersaturated solution is cooled.
9. Method according to 1 above, wherein the step d) of isolating the microparticles comprises at least one filtration and/or drying.
10. Method according to 1 above, wherein the temperature of the homogenous supersaturated solution of a substance in a crystallization medium in step c) is chosen lower if smaller micro-particle are to be generated and is chosen higher if larger micro-particle are to be generated.
11. Use of nanoparticles of a d50 between 10 nm and 999 nm as measured by Dynamic Light Scattering (DLS), laser diffraction or electron microscopy as seeding material in cooling crystallization.

In a preferred embodiment, the seeding material is characterized by a nano-particle size of a d90 between 10 nm and 999 nm as measured by Dynamic Light Scattering (DLS), laser diffraction or electron microscopy.

In a preferred embodiment, the d50 or d90 value which characterizes the nano-particles size of the seeding materials is measured by laser diffraction.

In a preferred embodiment of the method described herein the seeding material is provided at a concentration between 0.5 wt % to 30 wt %, preferably 0.9 wt % to 3 wt %, even more preferably 1 wt % to 2 wt %—wherein the weight percentage (wt %) is given with respect to total amount of the same substance the seeding material is composed of in the homogenous supersaturated solution of step a).

In a preferred embodiment of the method described herein the seeding material comprises at least one surfactant and at least one polymer i.e. a combination of stabilizers. For example the seeding material comprises one surfactant and two polymers as stabilizers.

In an alternative embodiment of the method described herein the seeding material comprises only one polymer as stabilizer.

In a further alternative embodiment of the method described herein the seeding material comprises only one surfactant as stabilizer.

The seeding material can be obtained by the method as described in WO 2021/069350. Said seeding material can be provided as powder or as tablet. Hence said powder or tablet comprises the seeding material characterized by a nano-particle size of a d50 between 10 nm and 999 nm as measured by Dynamic Light Scattering (DLS), laser diffraction or electron microscopy comprising at least one stabilizer, of step b) and said powder or table dissolves readily into the seeding material characterized by a nano-particle size of a d50 between 10 nm and 999 nm as measured by Dynamic Light Scattering (DLS), laser diffraction or electron microscopy comprising at least one stabilizer, of step b) upon contact with the homogenous supersaturated solution of step a) in step c) of the method described herein Due to the fact that the tablet readily dissolves into the seeding material characterized by a nano-particle size of a d50 between 10 nm and 999 nm as measured by Dynamic Light Scattering (DLS), laser diffraction or electron microscopy comprising at least one stabilizer, of step b) upon contact with the homogenous supersaturated solution of step a) in step c) of the method described herein, the duration of said step c) is comparable to the duration of step c) in cases where the seeding material is provided as suspension or as powder. Importantly, there is no substantial difference between the micro-particles generated with seeding material provided as suspension, as powder or as tablet.

If the provided seeding material is obtained by the methods as described in WO 2021/069350, the seeding material is obtained via A) suspending particles (of the substance) in an aqueous solution of a polymer;

B) drying the mixture obtained after step A);

characterized in that in step A), the d90 value of the particle size distribution is <1 μm, and in that prior to step B), the particles are contacted with an ionic surfactant and wherein the particles (of the substance) and the polymer are present in a weight ratio of ≥1:2 to <5:1 to each other. Preferably if the provided seeding material is obtained by this methods the polymer and the surfactant are present in a weight ratio of ≥10:1 to <300:1 to each other.

The seeding material obtained by the method of WO 2021/069350 as described above provided as powder or as tablet has the advantage that it can be stored more convenient than seeding material suspended in crystallization medium. Preferably, the nano-particles which are suspended in step A) of the method described in WO 2021/069350 and provided in step b) of the method described herein, respectively, are obtained via nano-grinding thereby providing a seeding material characterized by a nano-particle size of a d50 between 10 nm and 999 nm as measured by Dynamic Light Scattering (DLS), laser diffraction or electron microscopy comprising at least one stabilizer.

Suitable methods of nano-grinding (also termed nano grinding, nanogrinding or nanomilling) can be selected from the group consisting of wet bead milling in stirred media mills i.e. agitated ball mills, wet bead milling in planetary mills—especially suitable for small amounts- and high pressure homogenization.

Alternatively, the application of high shear forces in aqueous suspensions like in a high pressure homogenization process or the application of high impact forces between the particles like in a microfluidizer can be used to produce nano-particles.

To a skilled person it is clear that if nano grinding is used for providing the seeding material said nano grinding can only be performed if the nano-particles are not completely dissolved. Hence the skilled person would choose a suitable temperature within the temperature range of between 253 K and 323 K, preferably between 273 K and 303 K for nano-grinding the nano-particles in the aqueous suspension Preferably, if the nano-particles which are suspended in step A) of the method described in WO 2021/069350 are obtained in the form of particles by means of nano-grinding, a preferred nano-grinding time is observed during grinding in order to achieve better redispersion of the dried powder containing nanoparticles. This preferred grinding time (t-preferred) is significantly longer than the grinding time that would typically be required to achieve the necessary particle size. Preferably said preferred grinding time (t-preferred) is at least 1.5 times t0, preferably it is at least 2 times t0 and particularly preferably at least 4 times t0. Here, t0 is considered to be the usual grinding time at which the d90 value of the particle size distribution is 1.5 times the d90 value reached after 12 hours and is referred to as d90(12 h). In other words, this means that d90 (12 h) is ⅔ of the d90 value at the usual grinding time t0. Grinding time is understood to mean the residence time of the suspension in the mill, which explicitly means that the possible residence time of the suspension in an optionally present holding tank is not counted towards the grinding time, i.e. towards the comminution time (tz).

If the nano-particles provided in step b) of the method described herein, are provided suspended in a crystallization medium and obtained via nano-grinding, the grinding time is coupled to the d90 of the grinded suspension. The grinding can be stopped at once if the desired particle size is reached. Said nano-grinded seeding material comprising at least one stabilizer suspended in a crystallization medium can be used directly in step c) of the method described herein or can be stored. If the nano-grinded seeding material comprising at least one stabilizer suspended in a crystallization medium is stored it is preferably kept in the fridge at temperatures below 10° C. To enhance the stability of the particles, the nano suspensions can be dried. In this state the solid has to be stored 40° C. below the glass transition temperature of the used polymer.

The at least one stabilizer may be selected from polymers that sterically and/or surfactants that electrostatically or sterically stabilizes the nano-particles. Polymers and surfactants known to a skilled person include:

Alkyl celluloses, hydroxyalkyl celluloses, hydroxyalkylalkyl celluloses, carboxyalkyl celluloses, alkali metal salts of carboxyalkyl celluloses, carboxyalkylalkyl celluloses, carboxyalkyl cellulose esters, starches, pectins, chitin derivatives, polysaccharides, polyacrylic acid and its salts, polymethacrylic acid and its salts, polyvinyl alcohol, polyvinyl pyrrolidone, polyalkylene oxides, or a mixture of at least two of the above polymers. Preferably, the polymer is selected from methylcellulose, hydroxymethylcellulose, hydroxyethylcellulose, hydroxypropylcellulose (HPC), hydroxybutylcellulose, hydroxyethylmethylcellulose, hydroxypropylmethylcellulose (HPMC), carboxymethylcellulose, sodiumcarboxymethylcellulose, carboxymethylethylcellulose, carboxyalkylcellulose ester, starches, sodium carboxymethylamylopectin, chitosan, dextran sulfate sodium salt, alginic acid, alkali metal and ammonium salts of alginic acid, carrageenans, galactomannans, tragacanth, agar-agar, gum arabic, guar gum, xanthan gum, polyacrylic acid and its salts, polymethacrylic acid and its salts, polyvinyl alcohol, polyvinylpyrrolidone, polyethylene oxide, polypropylene oxide, copolymers of ethylene oxide and propylene oxide, N-vinylpyrrolidone-vinyl acetate copolymers or a mixture of at least two of the aforementioned polymers. Polyvinylpyrrolidones (especially K12 and K30 types) and N-vinylpyrrolidone-vinyl acetate copolymers are particularly preferred. The polymer can be a copolymer of ethylene oxide and propylene oxide, in particular a poloxamer, or a polyvinylpyrrolidone (PVP), in particular PVPK30 and PVP K12.

ionic surfactants such as anionic, cationic or zwitterionic (amphoteric) surfactants, wherein the ionic surfactant can be selected from acylamino acids (and salts thereof), such as: acylglutamates, for example sodium acylglutamate, di-TEA-palmitoylaspartate and sodium acaprylglutamate; acylpeptides, for example palmitoyl hydrolyzed milk protein, sodium cocoyl hydrolyzed soy protein and sodium/potassium cocoyl hydrolyzed collagen; Sarcosinates, for example, myristoyl sarcosine, TEA-lauroyl sarcosinate, sodium lauroyl sarcosinate and sodium cocoyl sarcosinate; Taurates, for example, sodium lauroyl taurate and sodium methyl cocoyl taurate; acyl lactylates, luroyl lactylate, caproyl lactylate, alaninates; carboxylic acids and derivatives, such as: carboxylic acids, for example lauric acid, aluminum stearate, magnesium alkanolate and zinc undecylenate; ester carboxylic acids, for example calcium stearoyl lactylate and sodium PEG lauramide carboxylate; Ether carboxylic acids, for example sodium laureth carboxylate and sodium PEG cocamide carboxylate; phosphoric acid esters and salts, such as DEA-oleth-phosphate and dilaureth-phosphate; sulfonic acids and salts, such as acyl-isethionates, e.g. sodium/ammonium cocoyl isethionate, alkyl aryl sulfonates, alkyl sulfonates, for example sodium coco monoglyceride sulfate, sodium C-olefin sulfonate, sodium lauryl sulfoacetate and magnesium PEG cocamide sulfate, sulfosuccinates, for example dioctyl sodium sulfosuccinate, disodium laureth sulfosuccinate, disodium lauryl sulfosuccinate and disodium undecylenamido MEA sulfosuccinate; as well as sulfuric acid esters, such as alkyl ether sulfate, for example sodium, ammonium, magnesium, MIPA, TIPA laureth sulfate, sodium myreth sulfate and sodium C-pareth sulfate, alkyl sulfates, for example sodium, ammonium and TEA lauryl sulfate OR cationic surfactants. such as alkylamines, alkylimidazoles, ethoxylated amines, quaternary surfactant, quaternary ammonium compounds, and esterquats, wherein quaternary surfactants contain at least one N atom covalently bonded to 4 alkyl or aryl groups, which leads, independent of the pH value, to a positive charge. Advantageously alkyl betaine, alkyl amidopropyl betaine and alkyl amidopropyl hydroxysulfaine are used. Quaternary ammonium compounds are, in particular benzyltrialkylammonium chlorides or bromides, such as benzyldimethylstearylammonium chloride, further alkyltrialkylammonium salts, for example cetyltrimethylammonium chloride or bromide, alkyldimethylhydroxyethylammonium chlorides or bromides, dialkyldimethylammonium chlorides or bromides, alkylamidethyltrimethylammonium ether salts, alkylpyridinium salts, for example lauryl- or cetylpyrimidinium chloride, imidazoline derivatives and compounds of cationic character such as amine oxides, for example alkyldimethylamine oxides or alkylaminoethyldimethylamine oxides or cetyltrimethylammonium.

Amphoteric surfactants can be Acyl/dialkyl ethylenediamines, for example sodium acylamphoacetate, disodium acylamphodipropionate, disodium alkylamphodiacetate, sodium acylamphohydroxypropyl sultonate, disodium acylamphodiacetate and sodium acylamphopropionate, and N-alkylamino acids, for example, aminopropylalkylglutamide, alkylaminopropionic acid, natuium alkylimidodipropionate and lauroamphocarboxyglycinate.

Preferred ionic surfactants include sodium dodecyl sulfate (SDS), sodium docusate (dioctyl sodium sulfosuccinate), sodium oleate and/or sodium deoxycholate.

Employing an ionic surfactant has the advantage that it further stabilizes the nano-particles in the seeding material electrostatically, Preferably the ionic surfactant is present in an amount of between 0.001 wt % and 10 wt % preferably 0.001 wt % and 0.4 wt %, most preferably between 0.01 wt % and 0.2 wt % in suspension.

Preferably the at least one stabilizer is used in a ratio of 1:1 to 10:1 (nanoparticle to stabilizer) preferably in a ratio of 10:3. A skilled person knows whether to use only one or more than one stabilizer in a given situation.

A preferred combination of polymer and surfactant are hydroxypropylmethylcellulose (HPMC) as polymer and sodium dodecyl sulfate (SDS) as surfactant.

A further preferred combination of polymers and surfactant are hydroxypropylcellulose (HPC) and polyvinylpyrrolidone (PVP) as polymers and sodium dodecyl sulfate (SDS) as surfactant.

Prior to optional step d) of the process described above the generated microparticles are present in the crystallization medium and said the suspension is herein referred to composition comprising microparticles.

In a preferred embodiment of the process described herein the substance provided as homogenous supersaturated solution is an active ingredient and hence the nano-particles and any generated micro-particles are active ingredient particles.

In an embodiment of step c) of bringing the homogenous supersaturated solution in contact with the seeding material occurs at a stirring rate of between 10 rpm to 600 rpm, more preferably of between 100 rpm to 500 rpm, even more preferably of between 300 to 400 rpm.

In another embodiment step c) of bringing the homogenous supersaturated solution in contact with the seeding material occurs at a temperature of between 30° C. and 115° C., preferably 40° C. and 100° C., even more preferably at between 45° C. and 92° C. the lower the seeding temperature, the smaller the final PSD (particle size distribution) obtained. All other crystallization parameters remain the same ones, only the temperature at which the system is seeded is changed.

In one embodiment of step c) of bringing the homogenous supersaturated solution in contact with the seeding material the temperature of the homogenous supersaturated solution of a substance in a crystallization medium in step c) is chosen lower if smaller micro-particle are to be generated and is chosen higher if larger micro-particle are to be generated.

Controlling the temperature in step c) is advantageous since it was found that the final particle size distribution could be controlled by selecting different seeding temperatures, while keeping the total amount of substance dissolved in the solution, the total amount of seeding material, and the particle size distribution of the seeding material constant. The system must be however kept within the metastable zone region, i.e. the window of temperature for which the system is supersaturated, but no spontaneous primary nucleation occurs. In detail it was shown that at a lower seeding temperature smaller product particles were generated, while at a higher seeding temperature larger product particles were generated. This effect is thought to be due to the size-dependent solubility typical of nano-size crystals, also known in the literature as Ostwald-Freundlich or Gibbs-Thomson effect (see for instance Iggland and Mazzotti, Cryst. Growth Des. 2011, 11, 10, 4611-4622). The exact tuning of the product particle size distribution depends on kinetics of particle nucleation, growth, and agglomeration of the particles of a given substance during step c) at a given temperature.

In a further embodiment after bringing the homogenous supersaturated solution in contact with the seeding material in step c) the solution is left ripening for between 10 min to 60 min, preferably for between 20 to 50 min most preferably for 30 min.

In a further preferred embodiment of the process described herein after bringing the homogenous supersaturated solution in contact with the seeding material the supersaturated solution is cooled thereby causing cooling crystallization.

The cooling parameters such as the cooling rate, the cooling time and the end point depend on a given process. A person skilled in the art knows how to define the optimal cooling rate using the solubility curve of a given homogenous supersaturated solution to determine how fast the solution has to be cooled, and for how long, to generate the optimal particle size distribution, maximize the final yields, and minimize the overall crystallization time, e.g. as detailed in the Crystallization Technology Handbook, Mersmann, CRC Press 2001.

Technical constraints that are taken into account by a skilled person in determining the cooling parameters are e.g. the maximum duty of the heat exchanger, together with further chemical, economical and/or planning considerations—such as maximum process time and product degradation. To find the optimal cooling parameters to be used for a given process under the given (equipment) conditions the residual supersaturation at the end of the process is measured for different cooling rates and different overall process times to determine the loss of yield with respect to the maximum theoretical value. Moreover, also the following parameters are measured with the method specified above to determine the optimal feasible cooling rate: final particle size distribution preferably together with polymorphic purity, filterability as well as chemical purity. As people skilled in the art know, the final particle size distribution affects the filterability of the product, which must therefore be also assessed. A standard practice to determine filterability is to measure the filter-cake resistance as expressed by the so-called "alpha-value". Further details can be found, for instance, in Filters and Filtration Handbook, 6th edition, Trevor and Chase, Butterworth-Heinemann 2015.

Hence due to practical and process constraints the typical time of cooling crystallization will be between 0,5 h and 8 h, preferably between 2 h and 5 h, most preferably around 3 h whereas the typical cooling rate will be between 0,05° C./minute and 10° C./minute preferably between 0.1° C./minute and 0.3° C./minute. In some cases, the cooling rate might not be constant but faster or slower during the process.

Devices for carrying cooling crystallizations are known in the art and are for example a curved impeller or Rush turbines, possibly in combination with baffles to increase the efficiency of mixing.

The stirring rate is adjusted for the specific mixer chosen, in order to maintain an equivalent specific energy input. The relevant nondimensional numbers, such as the Newton number, dependent on the type of mixer and on the presence/absences of baffles can be found by a person skilled in the art in the relevant published tables (e.g. in Perry Chemical Engineering Handbook, 8th Edition, McGraw-Hill, 2007).

In a preferred embodiment a curved impeller is used for the cooling crystallization. The specific energy input should be between 0.01 and 0.4 W/kg, preferably between 0.03 and 0.35 W/kg, most preferably 0.05 and 0.3 W/kg.

Preferably the stirring rate during cooling crystallization is the same as described above in the preferred embodiment of step c) of bringing the homogenous supersaturated solution in contact with the seeding material i.e. the preferred stirring rate during cooling crystallization is also between 100 rpm to 500 rpm, more preferably of between 200 rpm to 400 rpm, even more preferably of between 320 to 360 rpm.

In a further preferred embodiment of the process described herein step d) of isolating the microparticles comprises at least one filtration and/or drying.

Surprisingly it was found that the composition comprising microparticles had reasonable filtration characteristic, given the small particle size distribution, with alpha-values comprised between 1e12 and 1e13, comparable with those obtained with particles of sizes between 30 and 100 μm (d10 and d90, respectively) together with reasonable flowing ability (cf. Table 1). Such an outcome was unexpected as it had been speculated that the small size of the microparticles may lead to a significant degree of clumping.

In general, a person skilled in the art is aware of the different methods for drying compositions comprising microparticles such as spray drying or spray granulation.

When using spray drying, the composition comprising microparticles is introduced into a spray dryer and subjected to the drying process normally used in this apparatus. Optionally, also micrometer sized carrier particles like lactose or others can additionally be used during the drying process as it is usually done in solvent based drying processes and well described in the state of the art.

Moreover, what is described herein relates to the use of nanoparticles of a d50, preferably a d90 between 10 nm and 999 nm as measured by Dynamic Light Scattering (DLS), laser diffraction or electron microscopy as seeding material in cooling crystallization as it has been demonstrated for the first time that via employing nano-particles of a d50, preferably d90 between 10 nm and 999 nm as measured by Dynamic Light Scattering (DLS), laser diffraction or electron microscopy as seeding material leads to reproducible and controllable formation of microparticles comparable to microparticles produced using cooling crystallization with microparticles as seeding material but omitting the step of micronization. Hence this new use has the advantage that all drawbacks of micronization are overcome.

Figures

FIG. 1 shows that using nano seeding material (here active ingredient A) characterized by a nano-particle size of a d90 between 10 nm and 999 nm leads to micro-particles comparable to micro-particles generated with conventional processes.

Figure 2:
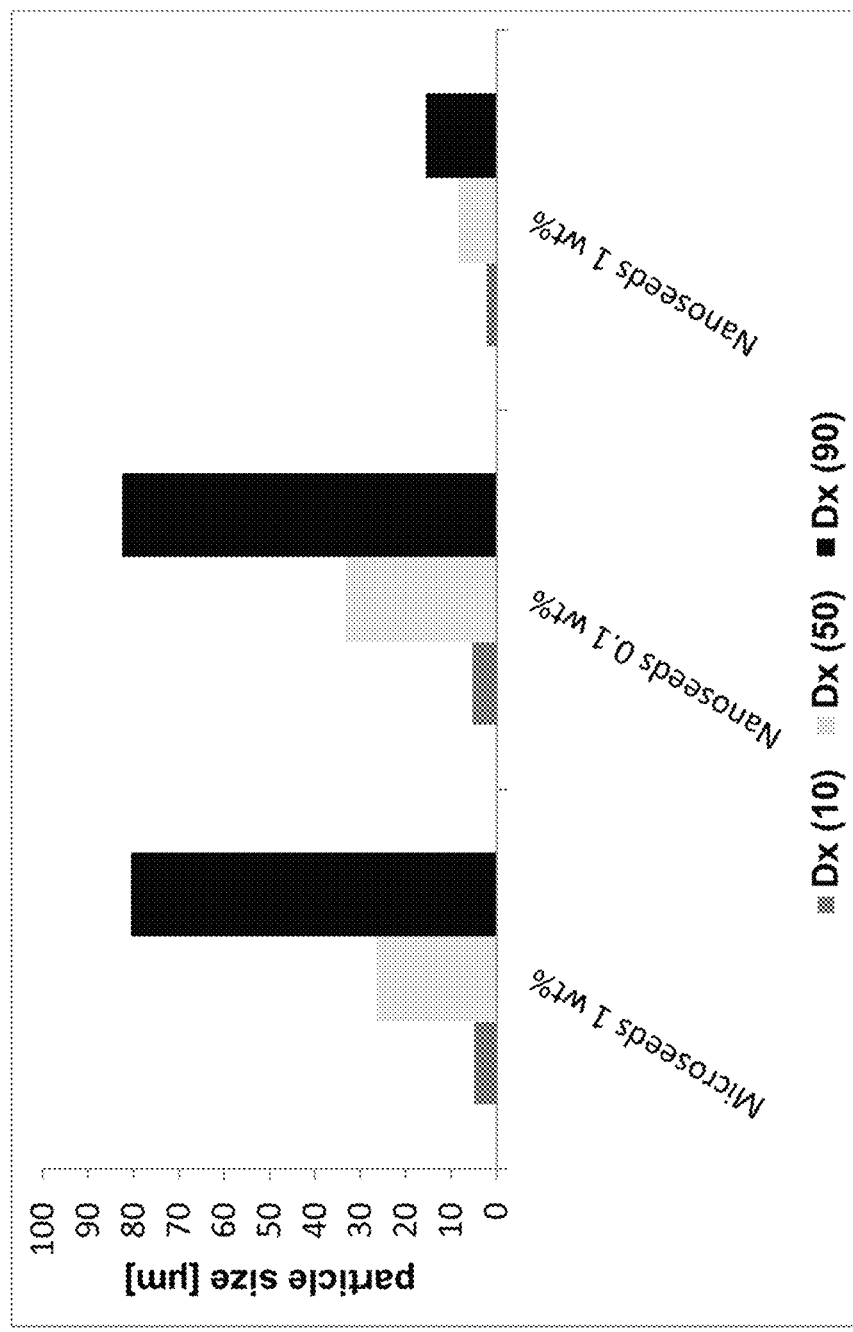
FIG. 2 depicts that less nano-seeding material is required to obtain a similar particle size distribution of the generated microparticles as with conventional processes.

FIG. 2 depicts that when using nano seeding material (here active ingredient A) characterized by a nano-particle size of a d90 between 10 nm and 999 nm only 10% of the seeding material quantity is needed compared to using seeding material with a d90 above 999 nm in order to obtain a similar particle size distribution of the generated microparticles.

Figure 3:
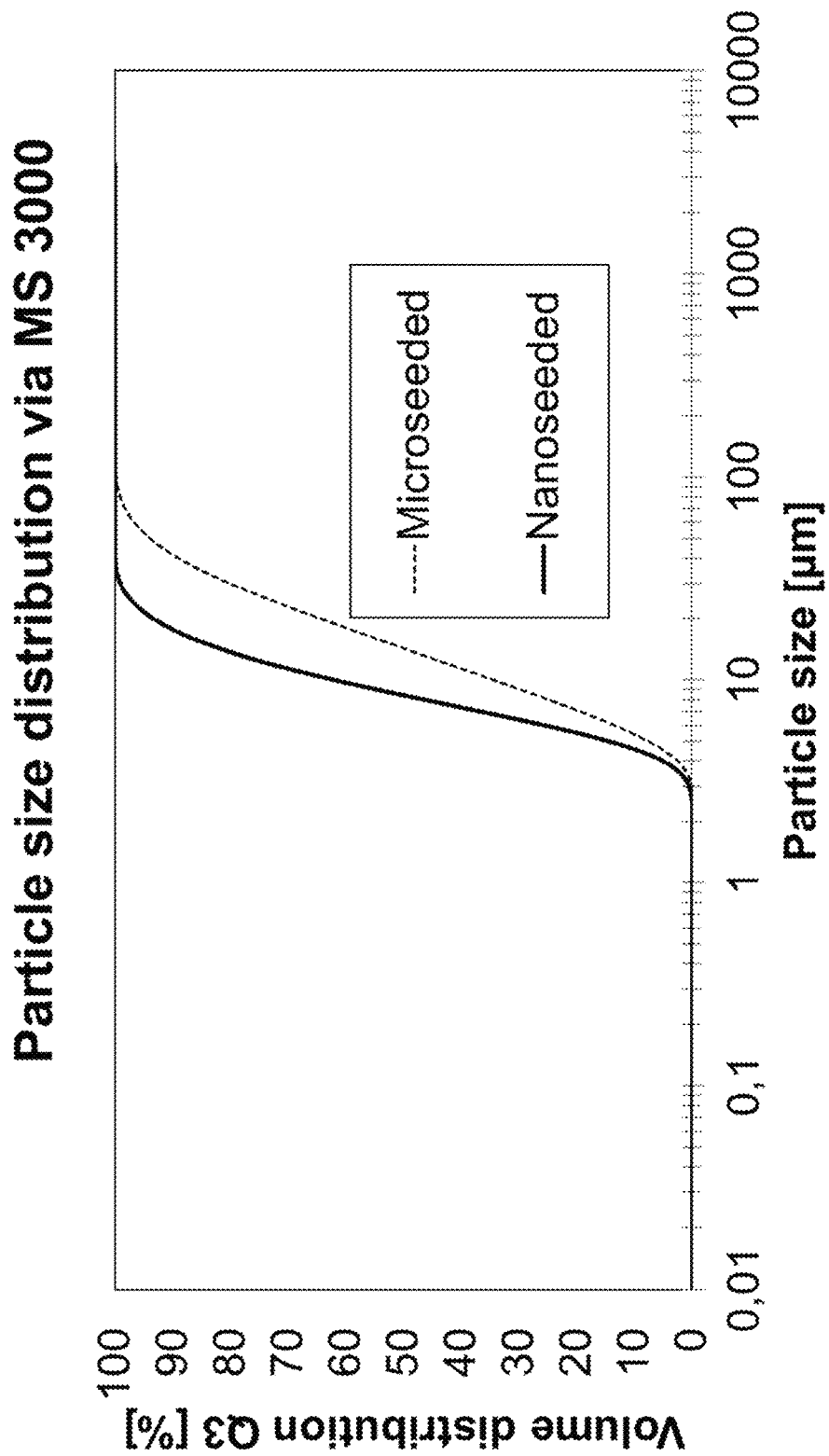
FIG. 3 shows that using nano seeding material (different active ingredient than the active ingredient of FIG. 1) leads to micro-particles comparable to micro-particles generated with conventional processes.

FIG. 3 shows that using nano seeding material (here active ingredient B) characterized by a nano-particle size of a d90 between 10 nm and 999 nm leads to micro particle typically obtained via conventional microseeding with subsequent micronization.

Figure 4:
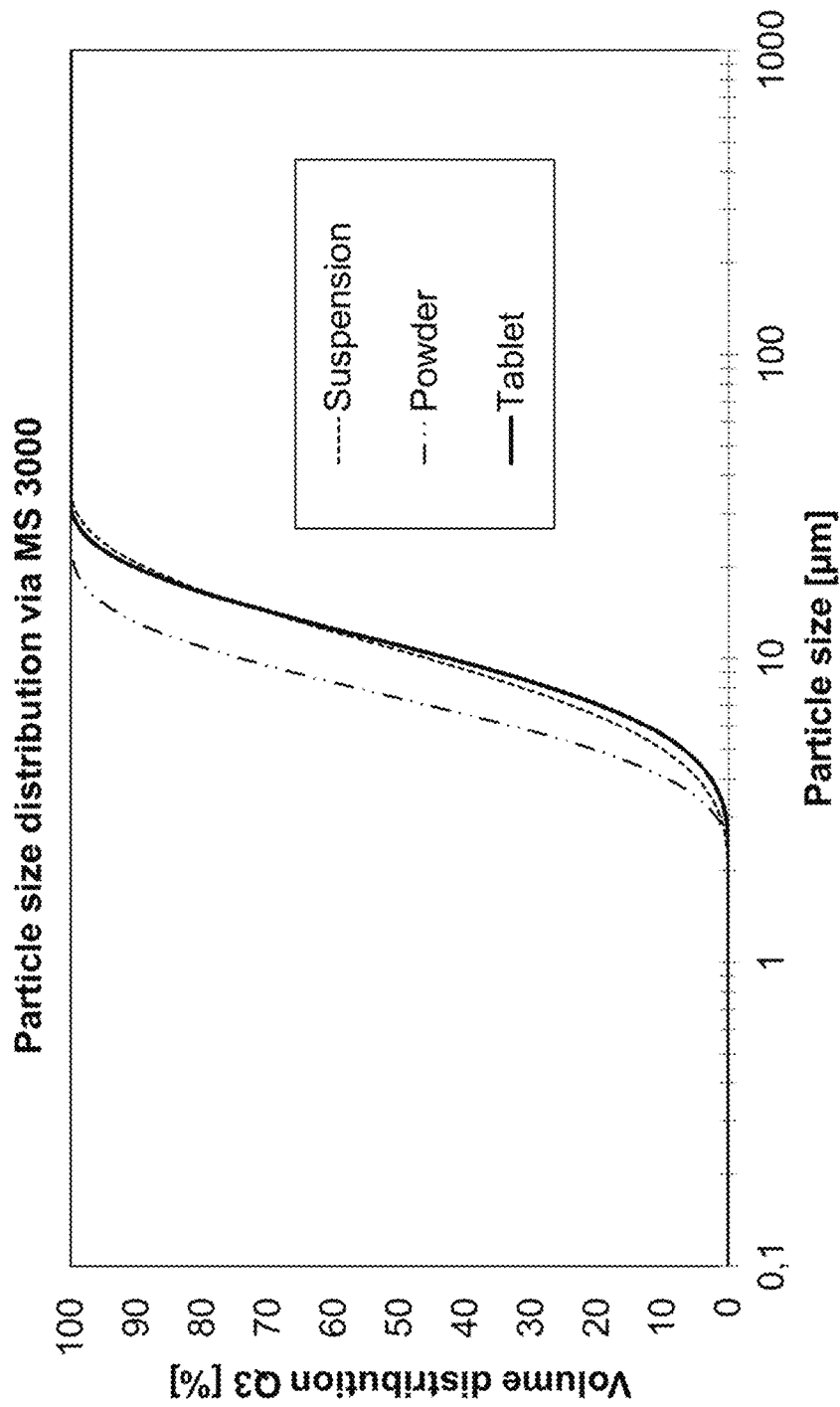
FIG. 4 shows that the type of nano-seeding material (suspension, powder or as tablet) does not play a key role in the crystallization process.

FIG. 4 shows that the nano seeding material can be stored as suspension, powder or as tablet and the microparticle generated with any of the three seeding material variants is comparable to the microparticles generated via conventional microseeding with subsequent micronization. When using powder generated according to example 1.2 below as seeding material the smallest microparticles were obtained.

Figure 5:
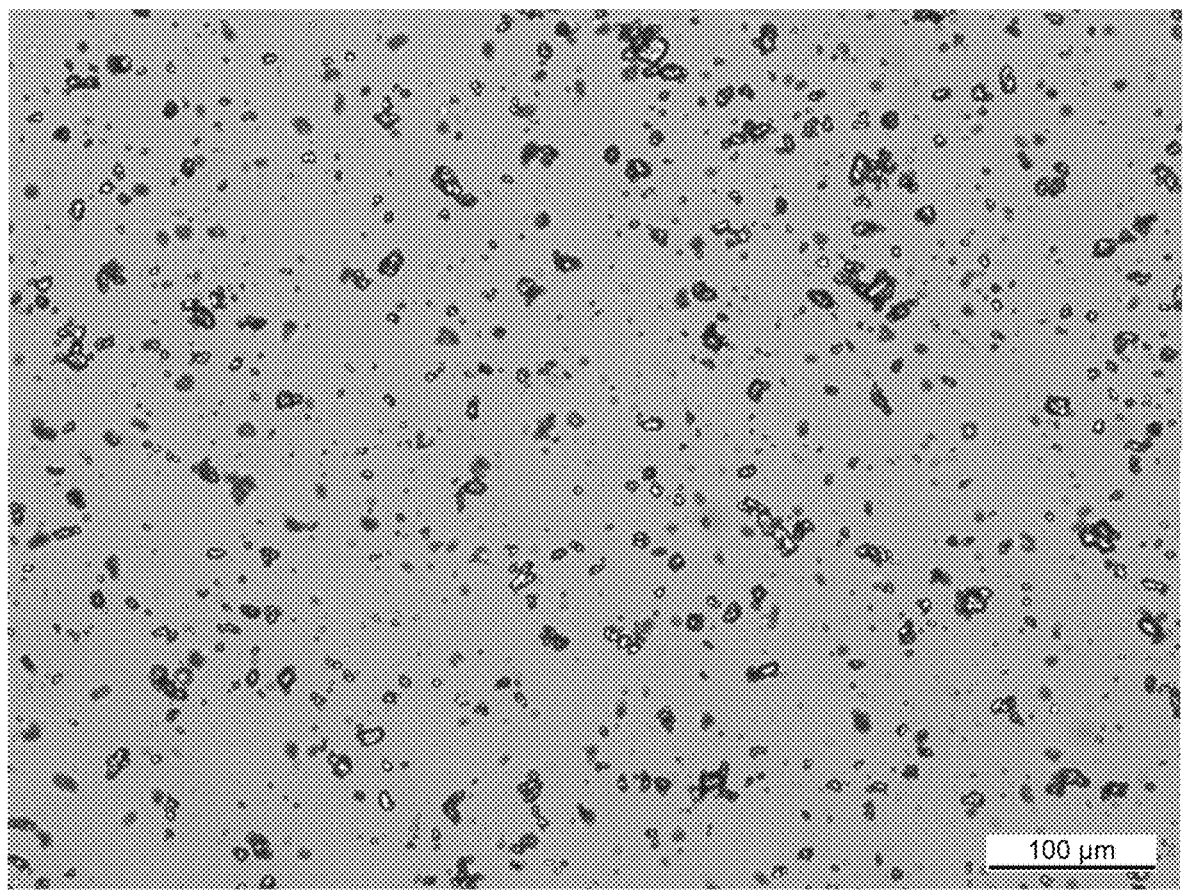
FIG. 5. depicts micro-particles generated with the method described herein on a 20 liter scale, i.e. it depicts the microparticles whose size distribution is shown in FIG. 8.

FIG. 5. shows that micro-particles generated with the method described herein on a 20 liter scale show a uniform size distribution and no agglomeration. The generated microparticles were active ingredient micro-particles obtained with seeding material comprising a combination of two polymers—here PVP 8 wt % and HPC 2 wt %— and a surfactant—here SDS 0.2 wt %)— as well as 10 wt % of the active ingredient (here active ingredient A).

Figure 6:
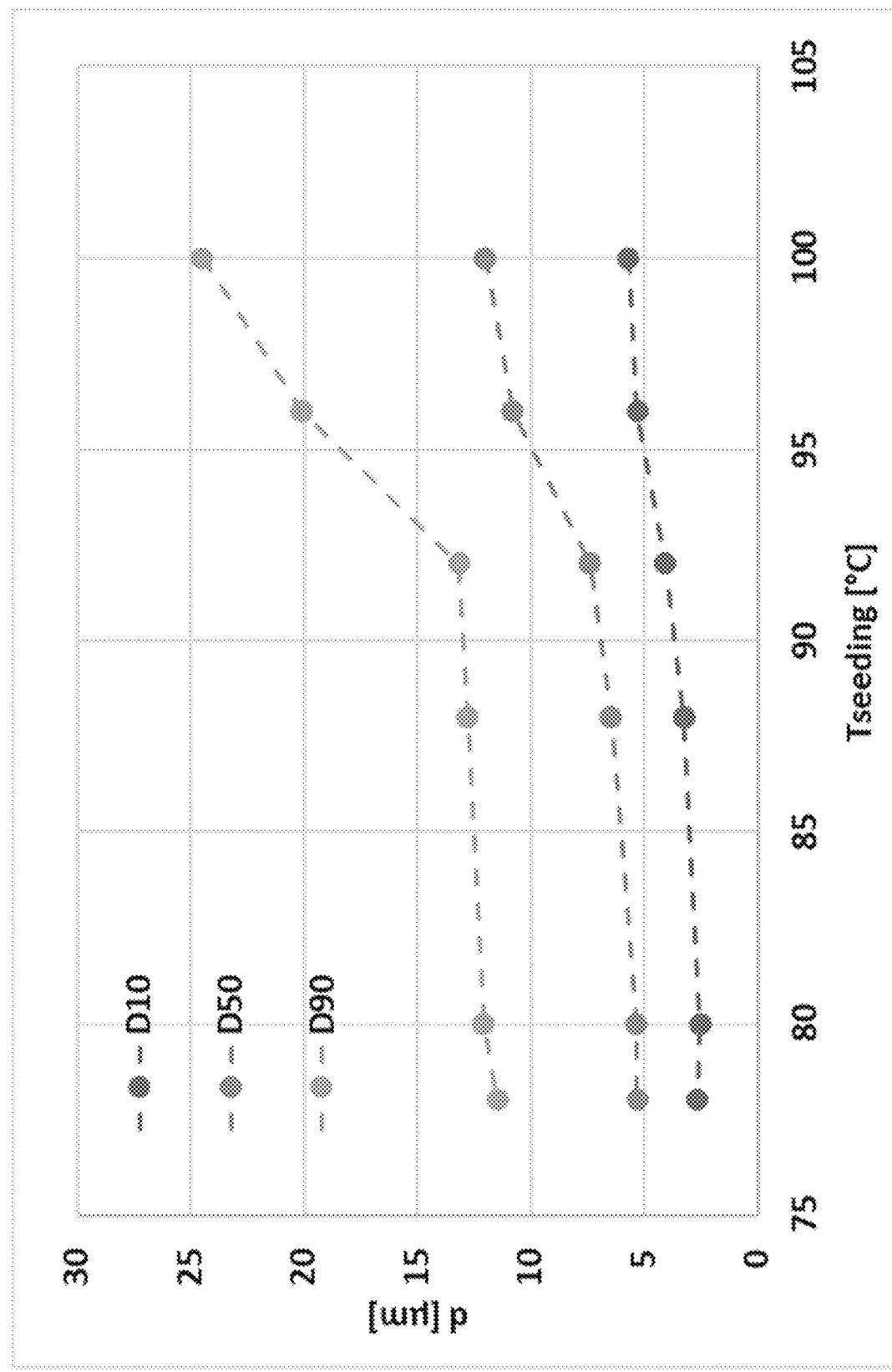
FIG. 6 shows the effect of the seeding temperature on the particle size distribution of the generated microparticles, as indicated by the measured d90, d50 and d10 values.
Figure 7:
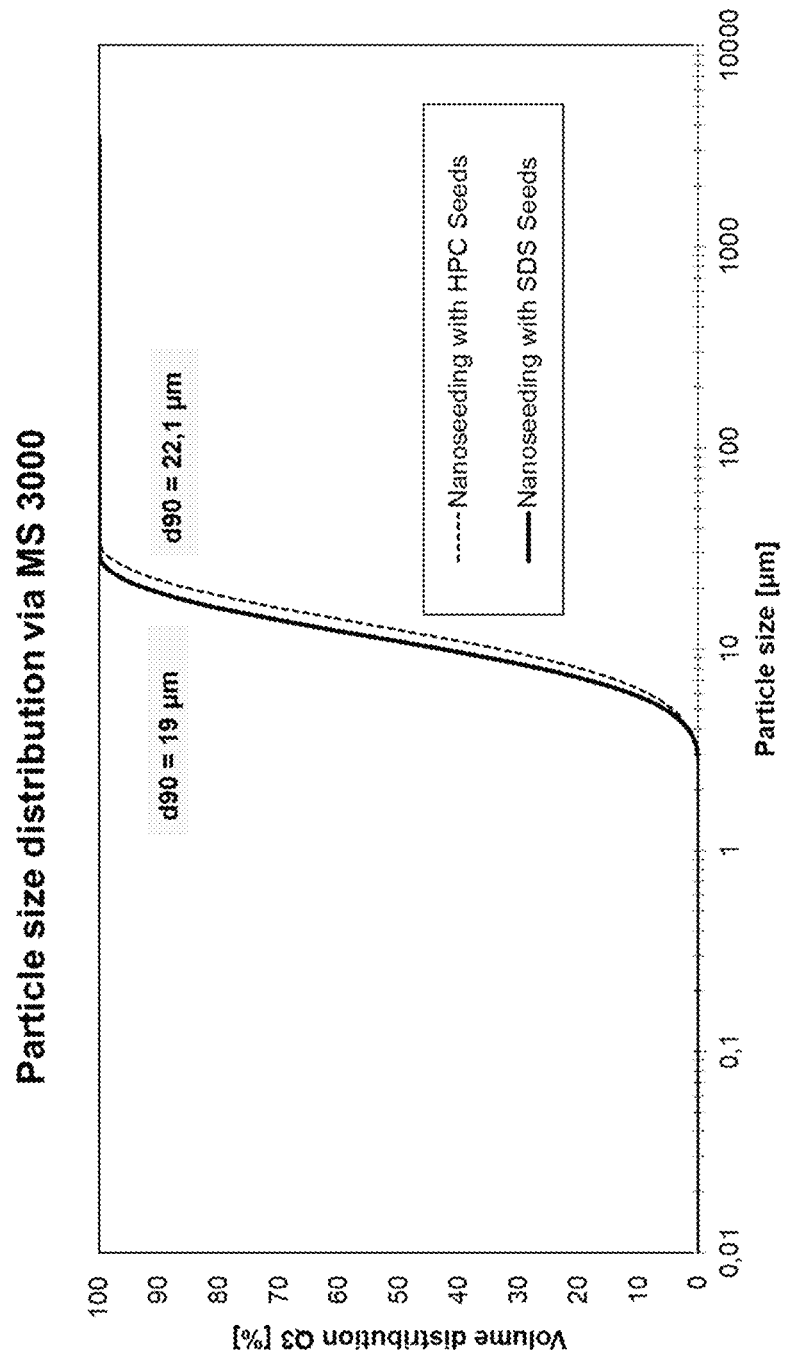
FIG. 7 shows that using seeding material comprising nanoparticles and a surfactant or a polymer (and not a combination of surfactant and polymer) leads to micro-particles comparable to micro-particles generated with conventional processes.

FIG. 6 shows the effect of the seeding temperature on the particle size distribution, as indicated by the measured d90, d50, d10. It can be seen that the lower the seeding temperature is, the smaller the final PSD (particle size distribution) of the microparticles that are obtained FIG. 7 shows that using nano seeding material characterized by a nano-particle size of a d50 between 10 nm and 999 nm comprising only a surfactant or only a polymer (and not a combination of surfactant and polymer) leads to microparticles comparable to micro-particles generated with conventional processes.

Figure 8:
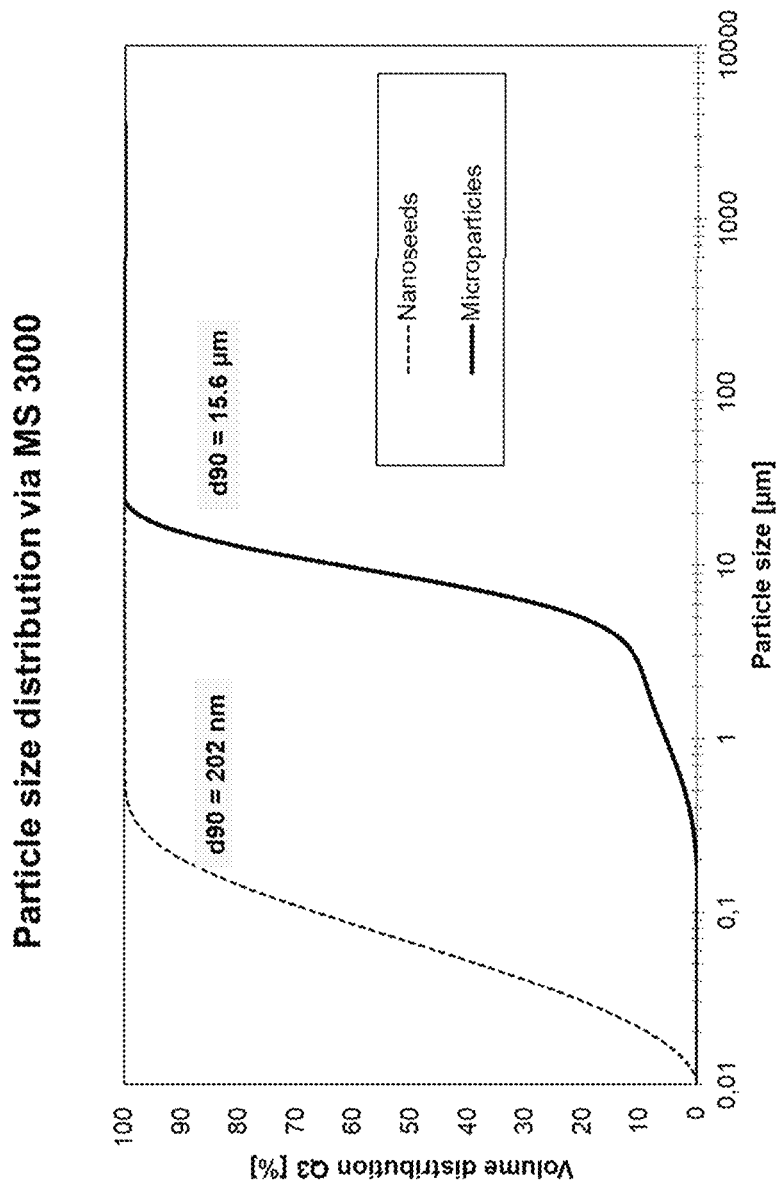
FIG. 8 shows that also on a 20 liter scale using nano seeding material leads to micro-particles comparable to micro-particles generated with conventional processes.

FIG. 8 shows that also on a 20 liter scale using nano seeding material leads to micro-particles comparable to micro-particles generated with conventional processes.

EXAMPLES

1. Generation of seeding material
1.1 Seeding material prepared in suspended state/Active ingredient A In this example the seeding material was obtained via nano-grinding of 10 wt % active ingredient microparticles in 86.9 wt-% water while adding 3 wt % HPMC and 0.1 wt % SDS in a Baler PML2 (small milling chamber) with a bead size of 0.1 mm (Yttrium stabilized Zirconium Oxide) for 40 min at 3000 rpm and a maximum temperature of 35° C. thereby obtaining suspended nano-particles. The seeding material was generated at a scale of 50 ml, 200 ml and 2000 ml.

Moreover seeding material was generated via nano-grinding of 10 wt % active ingredient microparticles in 79.8 wt % water while adding 2 wt % HPC, 8 wt % PVP and 0.2 wt % SDS in a Baler PML2 (small milling chamber) with a bead size of 0.1 mm (Yttrium stabilized Zirconium Oxide) for 40 min at 3000 rpm and a maximum temperature of 35° C. thereby obtaining suspended nano-particles. This seeding material was generated at a scale of 850 g.

1.2 Powder or tablet seeding material obtained by the method described in WO 2021/069350/Active Ingredient A In one example the seeding material was obtained via nano-grinding of 10 wt % active ingredient microparticles in 79.8 wt-% water while adding 8 wt % PVP K12 and 2 wt % HPC and 0.2 wt % SDS in a Baler PML2 (small milling chamber) with a bead size of 0.1 mm (Yttrium stabilized Zirconium Oxide) for 40 min at 3000 rpm and a maximum temperature of 35° C. thereby obtaining suspended nano-particles.

In the next step the suspension was spray dried in a ProCept Lab Spray Dryer with a nozzle diameter of 0.8 mm, a drying inlet temperature of T=110° C., an atomization pressure of 0.4 bar at a volume flow of 0.3 m$^3$/min and a feed flow of 5 g/min. The obtained powder was fully re-dispersible and part of the obtained powder was used as seeding material in the experiments described below. The rest of the obtained powder on the other hand was pressed to 150 mg tablets in a tablet press (StyleOne Medelpharm) at a tableting pressure of 100 MPa resulting in fully re-dispersible tablets. The powder and the tablet have the advantage, that they can be stored more easily and more stable that the material of 1.1. above.

Moreover seeding material was generated via nano-grinding of 10 wt % active ingredient microparticles in 80 wt % water while adding 2 wt % HPC, 8 wt % PVP and 0.2 wt % SDS in a Baler PML2 (small milling chamber) with a bead size of 0.1 mm (Yttrium stabilized Zirconium Oxide) for 40 min at 3000 rpm and a maximum temperature of 35° C. thereby obtaining suspended nano-particles. In the next step a part of the suspension was spray dried in a ProCept Lab Spray Dryer with a nozzle diameter of 0.8 mm, a drying inlet temperature of T=110° C., an atomization pressure of 0.4 bar at a volume flow of 0.3 m$^3$/min and a feed flow of 5 g/min. The obtained powder was fully re-dispersible and part of the obtained powder was used as seeding material in the experiments described below.

1.3 Seeding material as powder/Active ingredient B

In a further example a different active ingredient was used. Also in this example the seeding material was obtained via nano-grinding of 10 wt % active ingredient micropar-ticles in 79.8 wt-% water while adding 10 wt % PVP K12 0.2 wt % SDS in a Baler PML1 (small milling chamber) with a bead size of 0.1 mm (Yttrium stabilized Zirconium Oxide) for 40 min at 3000 rpm and a maximum temperature of 35° C. thereby obtaining suspended nano-particles.

In the next step the suspension was spray dried in a ProCept Lab Spray Dryer with a nozzle diameter of 0.8 mm, a drying inlet temperature of T=110° C., an atomization pressure of 0.4 bar at a volume flow of 0.3 m³/min and a feed flow of 5 g/min.

The obtained powder was fully redispersible and part of it was used as seeding material while the rest was pressed to tablets as described above under item 1.2 resulting in fully redispersible tablets.

1.4 Seeding material only comprising a polymer OR only comprising a surfactant

In a further example only a polymer—not a combination of at least one polymer and at least one surfactant—was used as stabilizer. In this example the seeding material was obtained via nano-grinding of 10 wt % active ingredient microparticles (active ingredient A) in 88 wt-% water while adding 2 wt % HPC in a planetary ball mill (Fritsch Pulverisette 5) at 400 rpm with beads with a size of 500 µm at a milling duration of 1.5 hours. The resulting nanoparticles had a stable particle size distribution at $d_{50}$=0,52 µm and at d90=881 nm The seeding material was generated at a scale of 15 ml.

The experiment was repeated using only SDS as stabilizer. The seeding material was also generated at a scale of 15 ml with a $d_{50}$=0,78.

2. Crystallization 2.1 Active Ingredient (A)

The seeding material obtained in example 1.1 was analyzed via Laser diffraction (MS3000 by Malvern) and was determined to have a d90 of 250 nm. The material was used within 12 hours from its production. During the intervening time, the seeding suspension was hold unstirred in a refrigerated environment (2° C.).

Then 1 wt-% with respect to total dissolved amount active ingredient of the seeding material obtained in example 1.1. was added to a vessel stirred by a curved impeller at 92° C. and a stirring rate of 350 rpm containing 100 ml of a homogenous supersaturated solution of the same active ingredient in the crystallization medium pure acetic acid. After seeding the system was left ripening for 30 min at constant temperature of 92° C. Afterwards the system was cooled in 3h at a constant cooling rate until 21° C. were reached. A sample of the crystallized active ingredient was analyzed via laser diffraction and optical microscopy.

The example was repeated on 20 liter scale using the seeding material comprising a combination of two polymers—here PVP 8 wt % and HPC 2 wt %—and a surfactant—here SDS (0.2 wt %)— as well as 10 wt % of the active ingredient A generated as described above under 1.2. The result is depicted in FIG. 5 and FIG. 8 and shows that also on a 20 liter scale using nano seeding material leads to micro-particles of a uniform size distribution without agglomerations comparable to microparticles generated with conventional processes.

2.2. Active Ingredient B

The seeding material obtained in example 1.3 was analyzed via Laser diffraction (MS3000 by Malvern) and was determined to have a d90 of 250 nm.

Then 1 wt-% (with respect to total dissolved amount active ingredient in a homogenous supersaturated solution) of the seeding material (powder) obtained in example 1.3. was added to a vessel stirred by a curved impeller at 45° C. and a stirring rate of 350 rpm containing a 50 ml homogenous supersaturated solution of the same active ingredient in the crystallization medium pure ethanol. After seeding the system was left ripening for 30 min at constant temperature of 45° C. Afterwards the system was cooled in 3h at a constant cooling rate until 5° C. were reached. Thereafter the system was left another 20 h at constant temperature of 5° C. A sample of the crystallized active ingredient B was analyzed via laser diffraction and optical microscopy.

2.3 Using seeding material comprising only a polymer OR only a surfactant

The crystallization of Active Ingredient A was performed twice—once with seeding material only comprising polymer and once with seeding material only comprising a surfactant—at similar operating conditions as reported above in 2.1 in an 100 mL reactor. Provided was an initially undersaturated solution of an active ingredient (active ingredient A) in crystallization medium (acetic acid) at 110° C. This undersaturated solution was cooled to 92° C. at which point the solution was supersaturated. Then seeding material comprising either only surfactant or only polymer as stabilizer obtained as described in 1.4 in form of a suspension was added to the system, in an amount corresponding to 2 wt-% with respect tothe total dissolved amount of active ingredient. After seeding the system was left ripening for 30 min at constant temperature of 92° C. Afterwards the system was cooled in 3h at a constant cooling rate until 21° C. were reached. A sample of the crystallized active ingredient A was analyzed via laser diffraction and optical microscopy. The results are depicted in FIG. 7 and demonstrated that the nano-seeding method described herein also works with seeding material only comprising one polymer or one surfactant.

2.5 Influence of seeding temperature on micro-particle size

The seeding material obtained in example 1.2 was analyzed via Laser diffraction (MS3000 by Malvern) and was determined to have a d90 of 250 nm. It was kept in storage in darkness inside a vial at Room Temperature (25° C.).

In order to assess the influence of seeding temperature on micro-particle size, 1 wt-% with respect to total dissolved amount active ingredient of the seeding material obtained in example 1.2 was added to a vessel stirred by a curved impeller at five different seeding temperatures: 100° C., 96° C., 92° C., 88° C., 80° C., 78° C. and a stirring rate of 350 rpm containing 100 ml of a homogenous supersaturated solution of the same active ingredient in the crystallization medium pure acetic acid. After seeding the system was left ripening for 30 min at constant temperature of 100° C., 96° C., 92° C., 88° C., 80° C., 78° C. respectively. Afterwards the system was cooled in 3h at a constant cooling rate until 21° C. were reached. A sample of the crystallized active ingredient was analyzed via laser diffraction and optical microscopy. A summary of the measured d90, d50, d10 are reported in FIG. 6., which shows that at a lower seeding temperature smaller product particles were generated, while at a higher seeding temperature larger product particles were generated.

3. Filtration 3.1 Active Ingredient A

Following crystallization as described in example 2.1 the composition comprising micrometer sized particles suspended in acetic acid was filtered through a fine-pored filter cloth in a pressure nutsch at room temperature. Thereafter rinsing with acetic acid 1:1 and then with water 6:1 at a pressure of 1 bar took place. The three filtration steps were examined and resulted in specific filter cake resistances of 4×1012, 8×1012 and 1×1013 which was an indicator for a good filterability.

3.2. Active Ingredient B

The suspension of active ingredient B obtained in example 2.1 was filtered in a common lab vacuum nutsch at room temperature using a fine-pored filter membrane without rinsing afterwards.

4. Drying 4.1 Active Ingredient A

Following filtration as described in example 3.1 the composition comprising active ingredient A micro-particles was dried in a Vacuum Mixer Dryer [Amixon VMT1] at 60° C. and a pressure <30 mbar for 3 hours.

4.2. Active Ingredient B

Following filtration as described in example 3.2 the composition comprising active ingredient B micro-particles was dried in a vacuum drying chamber at 30° C. and a pressure <30 mbar over night.

5 Characterization of the generated active ingredient micro-particles 5.1 Active ingredient A micro-particles The resulting micro-particles showed a comparable particle size distribution as conventionally obtained micro-particles (cf. FIG. 1) as determined by laser diffraction (MS3000 by Malvern, Hydro MV, wet dispersed in deionized water with Tween80 as surfactant to improve wetting and 180 seconds of ultrasonic treatment).

In detail FIG. 1 shows that using nano seeding material characterized by a nano-particle size of a d90 between 10 nm and 999 nm (left curve—solid line "Nanoseeds") leads to micro-particles (curve "Crystals produced with Nanoseeds) comparable to micro-particles generated with conventional processes i.e. employing microparticles as seeding material and subsequent micronization of the particles to achieve the desired particle size distribution (dotted line curve "Micronized Product"). In this example the nano seeding material was obtained as described in point 1.1 above Similar results were obtained with seeding material as described it item 1.2 above (data not shown).

TABLE

|  | Micronized particles | Nanoseeds | Nanoseeds (2L scale) |
|---|---|---|---|
| Flowability value (ffc) | 1.7 | <2 | 2.2 |

Thus, using nano seeding material characterized by a nano-particle size of a d90 between 10 nm and 999 nm (termed "Nanoseeds" in Table 1 above) on 300 ml scale (i.e. the volume of the homogenous supersaturated solution in step a) was 300 ml) leads to microparticle powder with a comparable flowability to microparticle powder obtained via conventional microseeding and subsequent micronizing Moreover, the same result was achieved at the lager 2L (i.e. the volume of the homogenous supersaturated solution in step a) was 2 L) scale.

Furthermore, as demonstrated in FIG. 2 it was found that when using nano seeding material characterized by a nano-particle size of a d90 between 10 nm and 999 nm only 10% of the seeding material quantity is needed compared to using seeding material with a d90 above 999 nm in order to obtain a similar particle size distribution of the generated microparticles. Thus, using nano seeding material characterized by a nano-particle size of a d90 between 10 nm and 999 nm as seeding material is more cost effective as significantly less seeding material is needed to generate the desired particle size distribution. This is also the case for nano-seeding material with a d50 between 10 nm and 999 nm. Also for this reason the method and use described herein are advantageous e.g. more cost-efficient. Without being bound by theory it is thought that as the nano seeding material provides for considerably more crystallization nuclei, a smaller overall quantity of the nano seeding material compared to conventional seeding material is required to obtain the same quantity of microparticles of the desired size. The seeding material was generated as described in example 1.1. above.

When using seeding material generated as described in example 1.2 above, it was found that in general the same results were obtained as with seeding material generated according to 1.1. but the using powder obtained according to 1.2 lead to even finer micrometer sized particles (cf. FIG. 4)

5.2 Characterization of the generated active ingredient B micro-particles

The characterization of the active ingredient B microparticles showed that also with this ingredient using a nano-particle size of a d90 between 10 nm and 999 nm prepared as described above in example 1.3 resulted in micro particles comparable to micro-particles generated with conventional processes i.e. employing microparticles as seeding material and subsequent micronization of the particles to achieve the desired particle size distribution (cf. FIG. 3).

Overall, it was found that using the method described herein the micronization step could be omitted and less seeding material was necessary to obtain a micro-particle powder comparable to the micro-particle powder derived from the conventional process.

The invention claimed is:

1. A method for generating micro-particles comprising:
   a) providing a homogenous supersaturated solution of a substance in a crystallization medium;
   b) providing a seeding material comprising a nano-particle size of a d50 between 10 nm and 999 nm as measured by Dynamic Light Scattering (DLS), laser diffraction or electron microscopy said seeding material comprising at least one stabilizer, wherein said seeding material is of the same substance as the substance of the homogenous supersaturated solution of a); and
   c) bringing the homogenous supersaturated solution in contact with the seeding material to generate the micro-particles.

2. The method of claim 1 wherein, the seeding material comprises a nanoparticle size of a d90 between 10 nm and 999 nm as measured by Dynamic Light Scattering (DLS), laser diffraction or electron microscopy.

3. The method of claim 1, wherein the seeding material comprises only one polymer as the at least one stabilizer.

4. The method of claim 1, wherein the seeding material comprises one surfactant and at least one polymer as the at least one stabilizer.

5. The method of claim 1, wherein the seeding material is provided suspended in the crystallization medium or is provided as seeding material obtained by
   A) suspending particles of the substance in an aqueous solution of a polymer;
   B) drying the mixture obtained after A);
   wherein
   in A), the d90 value of the particle size distribution is <1 μm, and wherein prior to B), the particles are contacted with an ionic surfactant and wherein the particles of the substance and the polymer are present in a weight ratio of ≥1:2 to <5:1 to each other.

6. The method of claim 5, wherein the seeding material is provided as powder or as tablet, which dissolves readily into seeding material comprising a nano-particle size of a d50 between 10 nm and 999 nm as measured by Dynamic Light Scattering (DLS), laser diffraction or electron microscopy, said seeding material comprising at least one stabilizer, and said seeding material dissolves upon contact with the homogenous supersaturated solution a).

7. The method of claim 1, wherein the substance provided as homogenous supersaturated solution is an active ingredient and the seeding material and any generated micro-particles are active ingredient particles.

8. The method of claim 1, where after bringing the homogenous supersaturated solution in contact with the seeding material, the supersaturated solution is cooled.

9. The method of claim 1, wherein the temperature of the homogenous supersaturated solution of a substance in a crystallization medium in c) is chosen lower if smaller micro-particle are to be generated and is chosen higher if larger micro-particle are to be generated.

10. The method of claim 1, further comprising isolating the micro-particles.

11. The method of claim 10, wherein said isolating the micro-particles comprises at least one filtration and/or drying.

* * * * *